US009848652B2

(12) United States Patent
Lin

(10) Patent No.: US 9,848,652 B2
(45) Date of Patent: Dec. 26, 2017

(54) COTTON-FREE ELECTRONIC CIGARETTE PREVENTING LIQUID SPILL

(71) Applicant: Guangrong Lin, Guangdong (CN)

(72) Inventor: Guangrong Lin, Guangdong (CN)

( * ) Notice: Subject to any disclaimer, the term of this patent is extended or adjusted under 35 U.S.C. 154(b) by 23 days.

(21) Appl. No.: 15/037,674

(22) PCT Filed: May 26, 2014

(86) PCT No.: PCT/CN2014/078417
§ 371 (c)(1),
(2) Date: May 18, 2016

(87) PCT Pub. No.: WO2015/081669
PCT Pub. Date: Jun. 11, 2015

(65) Prior Publication Data
US 2016/0295923 A1 Oct. 13, 2016

(30) Foreign Application Priority Data

Dec. 4, 2013 (CN) .......................... 2013 1 0640210

(51) Int. Cl.
*A24F 47/00* (2006.01)
*H02J 7/00* (2006.01)
(Continued)

(52) U.S. Cl.
CPC ........... *A24F 47/008* (2013.01); *A61M 15/06* (2013.01); *H02J 7/0042* (2013.01);
(Continued)

(58) Field of Classification Search
CPC ..... A24F 47/008; A61M 15/06; A61M 11/42; A61M 2205/3653; A61M 2205/8206
(Continued)

(56) References Cited

U.S. PATENT DOCUMENTS 8,899,240 B2 * 12/2014 Mass ..................... A61M 15/06
131/194
2007/0267031 A1 * 11/2007 Hon ..................... A24F 47/008
131/273
(Continued)

FOREIGN PATENT DOCUMENTS

CN 201108029 Y 9/2008
CN 102326869 A 1/2012
(Continued)

OTHER PUBLICATIONS

International Search Report of PCT Patent Application No. PCT/CN2014/078417 dated Sep. 1, 2014.
(Continued)

*Primary Examiner* — Harshad C Patel

(57) ABSTRACT

Disclosed is a cotton-free electronic cigarette preventing liquid spill, comprising a vaporizer assembly, a mouthpiece assembly and a battery control assembly. The vaporizer assembly comprises an outer sleeve, a liquid storage cup, a vaporizer unit and a heat insulation sleeve. An air passage is formed between an exterior longitudinal flat surface of the liquid storage cup and the heat insulation sleeve. The liquid storage cup is sheathed with the outer sleeve, an inner wall of the outer sleeve and an exterior arc surface of the liquid storage cup forms an arc-shaped slit. An inner wall of the outer sleeve and the exterior longitudinal flat surface of the liquid storage cup forms a vapor flow passage. The vapor flow passage is interconnected to the arc-shaped slit. The mouthpiece assembly is fixed to one end of the outer sleeve to seal an outlet of the arc-shaped slit.

9 Claims, 6 Drawing Sheets

(51) Int. Cl.
*A61M 15/06* (2006.01)
*A61M 11/04* (2006.01)

(52) U.S. Cl.
CPC ... *A61M 11/042* (2014.02); *A61M 2205/3653* (2013.01); *A61M 2205/8206* (2013.01)

(58) Field of Classification Search
USPC .................. 131/329, 360, 236, 328
See application file for complete search history.

(56) References Cited

U.S. PATENT DOCUMENTS

| | | | | |
|---|---|---|---|---|
| 2010/0200008 | A1* | 8/2010 | Taieb | A24F 47/008 131/360 |
| 2011/0011396 | A1* | 1/2011 | Fang | A24F 47/008 128/202.21 |
| 2013/0192618 | A1* | 8/2013 | Li | A24F 47/008 131/329 |
| 2013/0199528 | A1* | 8/2013 | Goodman | F22B 1/282 128/203.26 |
| 2014/0196734 | A1* | 7/2014 | Liu | A24F 47/008 131/329 |

FOREIGN PATENT DOCUMENTS

| | | |
|---|---|---|
| CN | 202714190 U | 2/2013 |
| CN | 202873796 U | 4/2013 |
| CN | 103355745 A | 10/2013 |
| CN | 103653259 A | 3/2014 |
| CN | 103653260 A | 3/2014 |
| CN | 203563694 U | 4/2014 |
| CN | 203563696 U | 4/2014 |

OTHER PUBLICATIONS

1st Office Action of counterpart Chinese Patent Application No. 201310640210.2 dated Jun. 11, 2015.

* cited by examiner

COTTON-FREE ELECTRONIC CIGARETTE PREVENTING LIQUID SPILL

FIELD OF THE INVENTION

The present invention relates to a cotton-free electronic cigarette, especially relates to a cotton-free electronic cigarette that can effectively prevents liquid spill.

BACKGROUND OF THE INVENTION

With the development of electronic cigarettes, various electronic cigarettes with different structures have been invented. Among these electronic cigarettes, a cotton-free electronic cigarette is a highly popular electronic cigarette right now. The cotton-free electronic cigarette has fewer components than conventional electronic cigarettes, so the assembly of the components of the cotton-free electronic cigarette is easy and the assembled cotton-free electronic cigarette has a simple structure. The cotton-free electronic cigarette uses a liquid percolation piece to directly absorb cigarette liquid, due to temperature difference and/or other reasons, residual vapor easily condenses to form residual liquid, which will be inhaled into a user's mouth if a vapor flow passage of the cotton-free electronic cigarette is arranged in the middle of the cotton-free electronic cigarette to directly reach a mouthpiece. In this aspect, the cotton-free electronic cigarette is inferior to conventional cotton-bearing electronic cigarettes in preventing liquid spill, because cigarette liquid absorption cotton of the conventional cotton-bearing electronic cigarette is able to absorb residual liquid. Thus, how to improve the structure of existing cotton-free electronic cigarette to effectively prevent liquid spill is a problem to be solved.

SUMMARY OF THE INVENTION

In order to overcome the shortcomings of existing cotton-free electronic cigarette, the present invention aims to provide a novel cotton-free electronic cigarette that stores residual liquid produced during inhaling by an arc-shaped slit, thereby preventing the problem of liquid spill in existing cotton-free electronic cigarettes.

The technical solution of the present invention is a cotton-free electronic cigarette preventing liquid spill, comprising a mouthpiece assembly, a battery control assembly and a vaporizer assembly, the mouthpiece assembly and the battery control assembly being respectively connected to two ends of the vaporizer assembly, characterized in that the vaporizer assembly comprises:

an outer sleeve, the outer sleeve being a pipe having an inner diameter larger than an outer diameter of a liquid storage cup of the cotton-free electronic cigarette, the liquid storage cup, the liquid storage cup being a cylinder having a segmental-circular cross section formed by an exterior longitudinal flat surface, an exterior surface of an outlet end of the liquid storage cup being provided with a bayonet, the bayonet being configured to be fitted into a heat insulation sleeve, a vaporizer unit, the vaporizer unit comprising an electric heating assembly and a power connecting assembly, and the heat insulation sleeve, the heat insulation sleeve having a tubular structure.

The liquid storage cup stores cigarette liquid therein, an opening of the liquid storage cup is provided with a liquid percolation piece and a filter piece; the vaporizer unit is placed inside the heat insulation sleeve; the exterior longitudinal flat surface of the liquid storage cup forms an air passage when the bayonet of the liquid storage cup is fitted into the heat insulation sleeve; the liquid storage cup is sheathed with the outer sleeve, an inner wall of the outer sleeve and an exterior arc surface of the liquid storage cup forms an arc-shaped slit, the arc-shaped slit being used for preventing spill of residual condensed cigarette liquid; an inner wall of the outer sleeve and the exterior longitudinal flat surface of the liquid storage cup forms a vapor flow passage, the vapor flow passage is interconnected to the arc-shaped slit; the mouthpiece assembly is fixed to one end of the outer sleeve to seal an outlet of the arc-shaped slit, such that an inhalation hole of the mouthpiece assembly is interconnected to the vapor flow passage.

The mouthpiece assembly is mainly consisted of a mouthpiece, the mouthpiece is inserted into said one end of the outer sleeve, the inhalation hole of the mouthpiece assembly is arranged in the middle of the mouthpiece, an interior end of the mouthpiece has an annular groove, the annular groove is positioned between the inhalation hole and the vapor flow passage so as to further prevent liquid spill.

The segmental-circular cross section of the liquid storage cup which is formed by the exterior longitudinal flat surface is encircled by the arc-shaped slit.

The outer sleeve receives the battery control assembly to form a disposable electronic cigarette.

Alternatively, the other end of the outer sleeve is connected with the battery control assembly through a connecting piece to form an electronic cigarette having a replaceable vaporizer assembly.

The electric heating assembly comprises an electric heating element and a supporting frame, the electric heating element is fitted into the supporting frame and is arranged to correspond to the filter piece to atomize cigarette liquid.

The power connecting assembly comprises an insulation ring and a needle electrode, the needle electrode passes through the insulation ring and the supporting frame to be finally electrically connected to the electric heating element.

The battery control assembly is connected to a bottom of the supporting frame through a fixation seat.

The exterior longitudinal flat surface of the liquid storage cup is a rectangle.

The width of the arc-shaped slit is from 0.05 mm to 0.8 mm.

The technical solutions of the present invention have the following advantages. The liquid storage cup has an exterior longitudinal flat surface and has an outer diameter smaller than an inner diameter of the outer sleeve. Therefore, the vapor flow passage and the arc-shaped slit are formed when the liquid storage cup is sheathed with the outer sleeve, wherein the vapor flow passage and the arc-shaped slit are intercommunicate. The mouthpiece assembly seals an outlet of the arc-shaped slit, as a result, when the produced vapor passes into the vapor flow passage and the arc-shaped slit, some of the produced vapor will be condensed to form residual liquid, and the residual liquid will be adsorbed in the arc-shaped slit due to the narrow space of the arc-shaped slit. Therefore, the condensed residual liquid will not be inhaled into the user's mouth. From the above, by the arrangement of the vapor flow passage and the arc-shaped slit, the cotton-free electronic cigarette of the present invention solves the problem of liquid spill in existing cotton-free electronic cigarettes.

DETAILED DESCRIPTION OF ILLUSTRATED EMBODIMENTS

Figure 1:
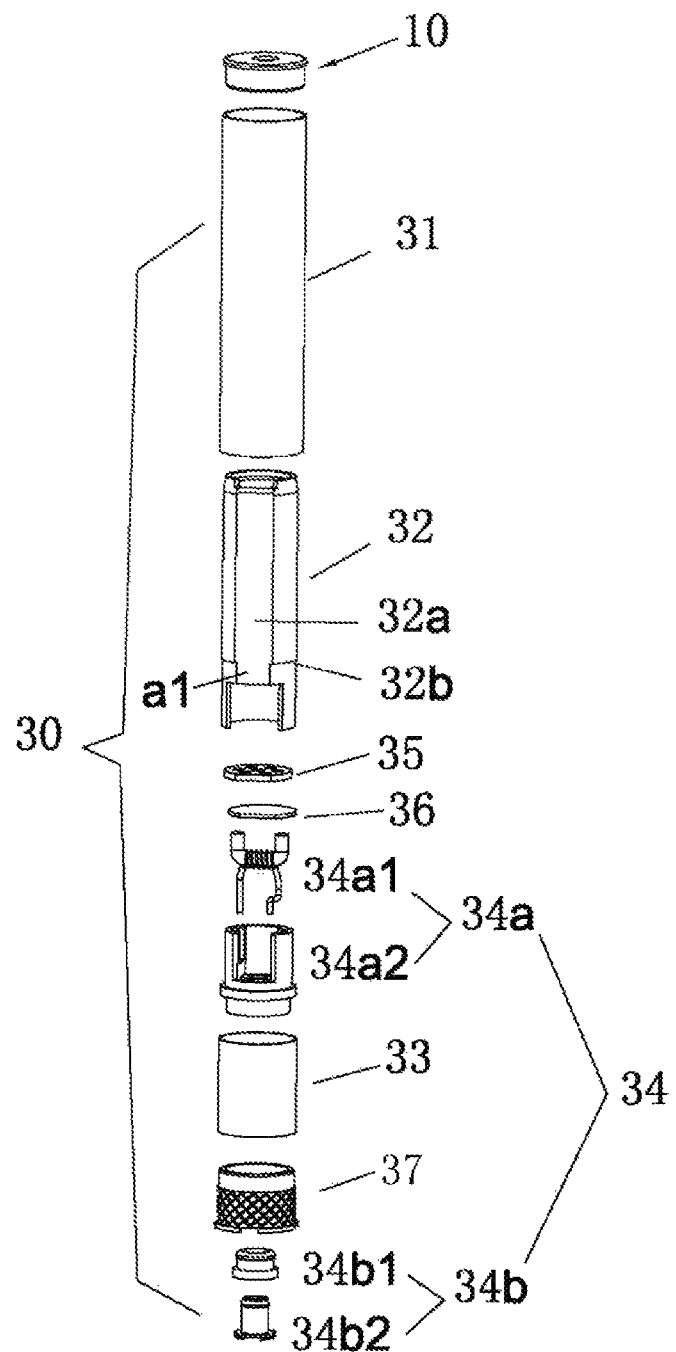
FIG. 1 is a perspective exploded view showing a vaporizer assembly and a mouthpiece assembly of the present invention.
Figure 2:
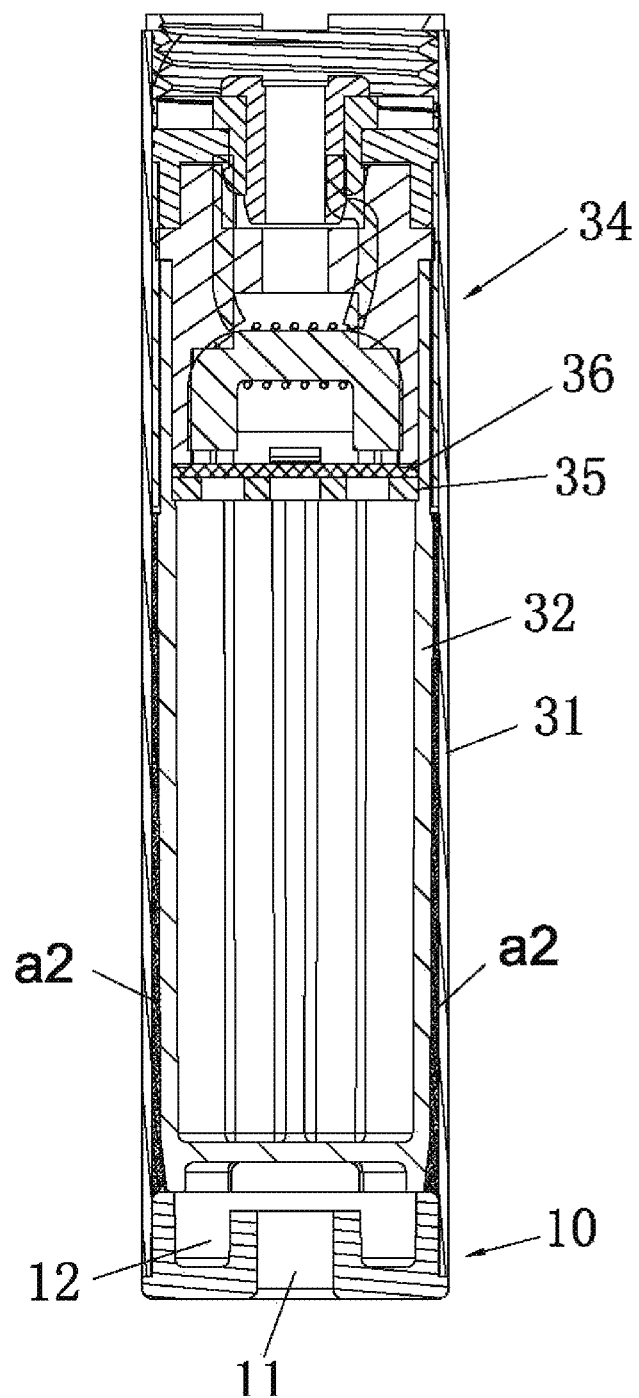
FIG. 2 is a cross-sectional view of a vaporizer assembly and a mouthpiece assembly of the present invention, showing an arc-shaped slit of the present invention.
Figure 3:
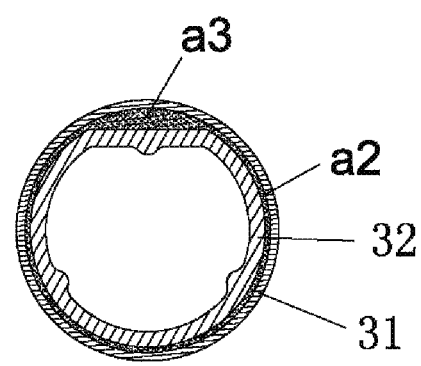
FIG. 3 is a cross-sectional view of a vaporizer assembly of the present invention.
Figure 4:
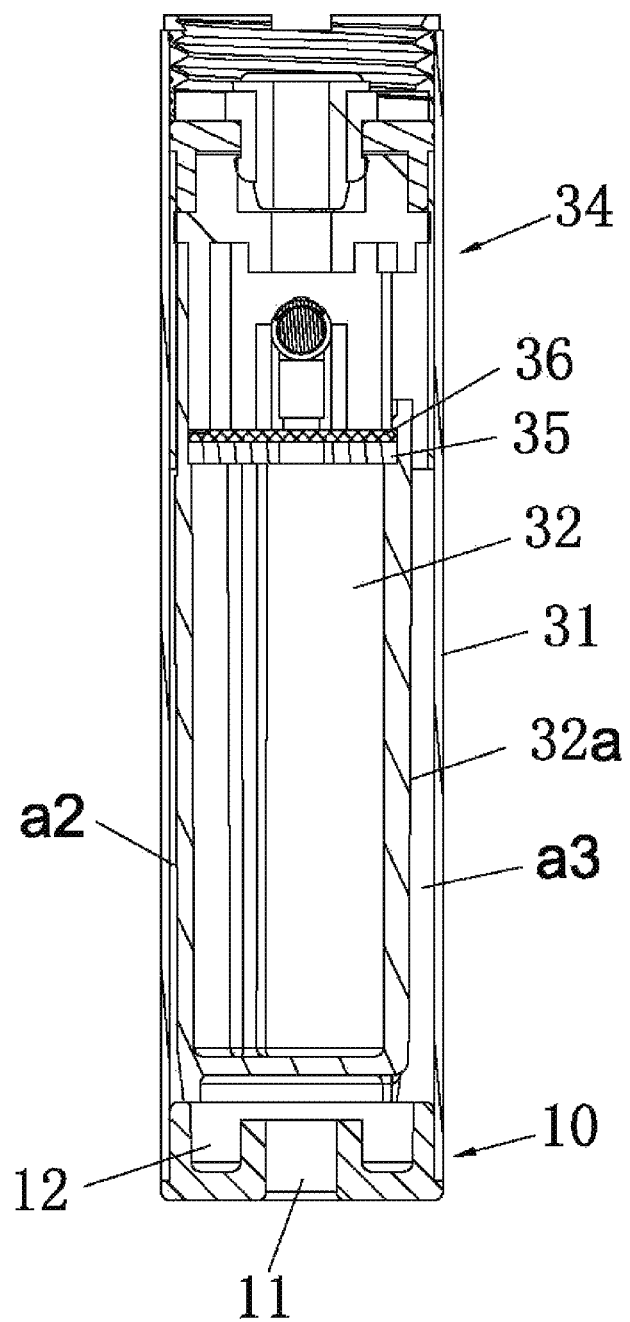
FIG. 4 is a cross-sectional view of a vaporizer assembly and a mouthpiece assembly of the present invention, showing a vapor flow passage of the present invention.
Figure 5:
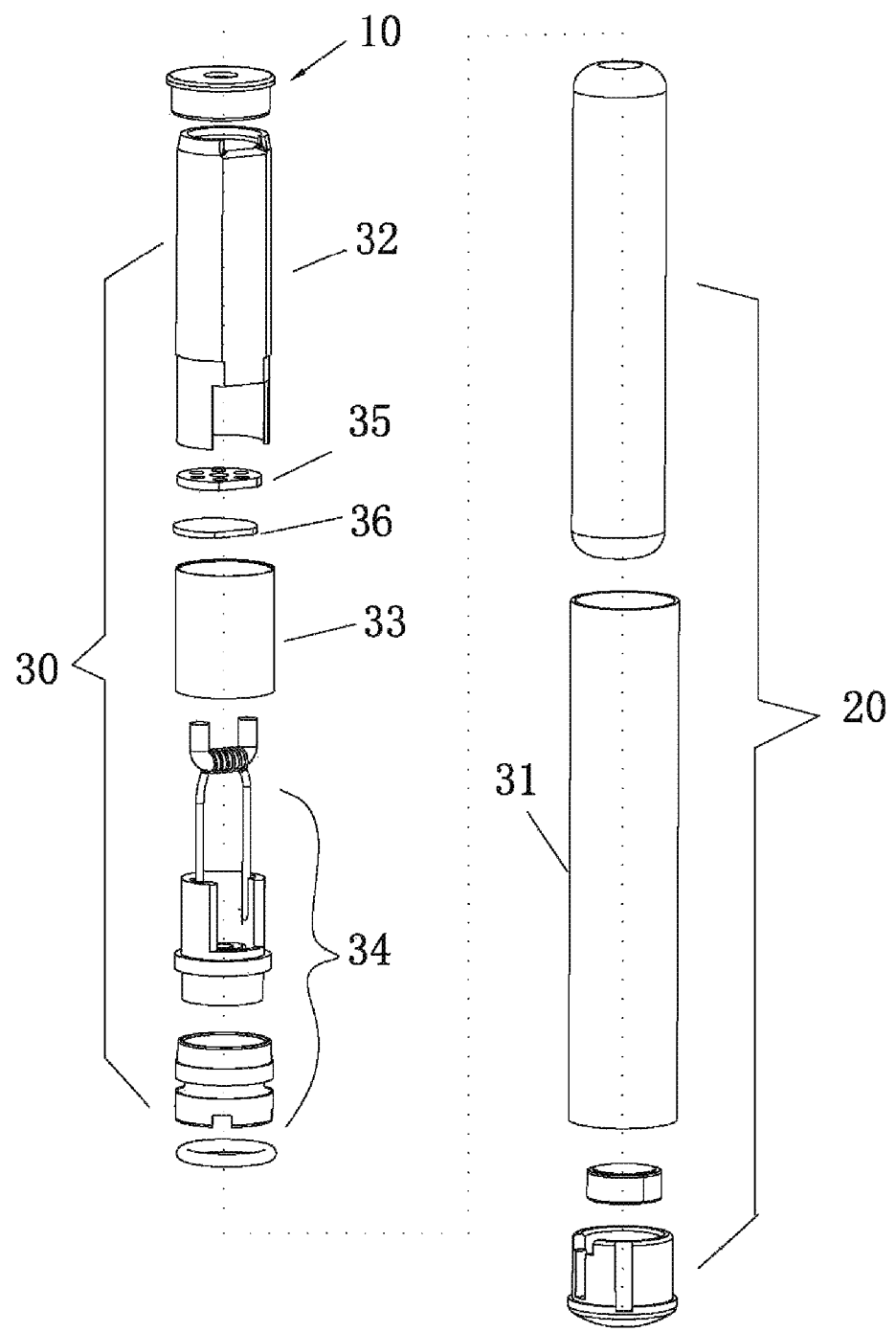
FIG. 5 is a perspective exploded view of a cotton-free electronic cigarette of the present invention.
Figure 6:
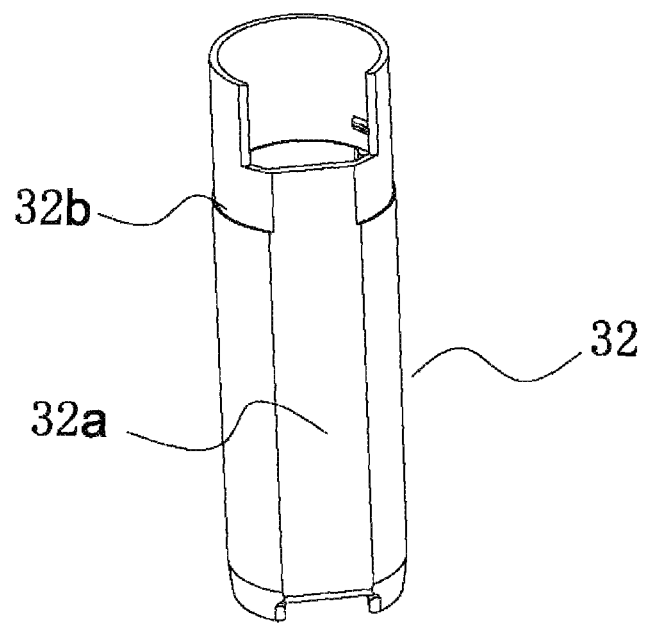
FIG. 6 is a perspective view of a liquid storage cup of the present invention.

As shown in FIGS. 1-6, a cotton-free electronic cigarette preventing liquid spill comprises a mouthpiece assembly 10, a battery control assembly 20 and a vaporizer assembly 30. The mouthpiece assembly 10 and the battery control assembly 20 are respectively connected to two ends of the vaporizer assembly 30. The vaporizer assembly 30 comprises:

an outer sleeve 31, the outer sleeve 31 being a pipe having an inner diameter larger than an outer diameter of a liquid storage cup 32 of the cotton-free electronic cigarette;

the liquid storage cup 32, the liquid storage cup 32 being a cylinder having a segmental-circular cross section formed by an exterior longitudinal flat surface 32a, an exterior surface of an outlet end of the liquid storage cup 32 being provided with a bayonet 32b, the bayonet 32b being configured to be fitted into a heat insulation sleeve 33;

a vaporizer unit 34, the vaporizer unit 34 comprising an electric heating assembly 34a and a power connecting assembly 34b; and the heat insulation sleeve 33, the heat insulation sleeve 33 having a tubular structure.

The liquid storage cup 32 stores cigarette liquid therein, an opening of the liquid storage cup 32 is provided with a liquid percolation piece 35 and a filter piece 36; the vaporizer unit 34 is placed inside the heat insulation sleeve 33; the exterior longitudinal flat surface 32a of the liquid storage cup 32 forms an air passage a1 when the bayonet 32b of the liquid storage cup 32 is fitted into the heat insulation sleeve 33; the liquid storage cup 32 is sheathed with the outer sleeve 31, an inner wall of the outer sleeve 31 and an exterior arc surface of the liquid storage cup 32 forms an arc-shaped slit a2, the arc-shaped slit a2 being used for preventing spill of residual condensed cigarette liquid; an inner wall of the outer sleeve 31 and the exterior longitudinal flat surface 32a of the liquid storage cup 32 forms a vapor flow passage a3, the vapor flow passage a3 is interconnected to the arc-shaped slit a2; the mouthpiece assembly 10 is fixed to one end of the outer sleeve 31 to seal an outlet of the arc-shaped slit a2, such that an inhalation hole 11 of the mouthpiece assembly 10 is interconnected to the vapor flow passage a3.

The mouthpiece assembly 10 is mainly consisted of a mouthpiece, the mouthpiece is inserted into said one end of the outer sleeve 31, the inhalation hole 11 of the mouthpiece assembly 10 is arranged in the middle of the mouthpiece, an interior end of the mouthpiece has an annular groove 12, the annular groove 12 is positioned between the inhalation hole 11 and the vapor flow passage a3 so as to further prevent liquid spill.

The segmental-circular cross section of the liquid storage cup 32 which is formed by the exterior longitudinal flat surface 32a is encircled by the arc-shaped slit a2.

The battery control assembly 20 is installed within the outer sleeve 31 to form a disposable electronic cigarette.

Alternatively, the other end of the outer sleeve 31 is connected with the battery control assembly 20 through a connecting piece to form an electronic cigarette having a replaceable vaporizer assembly.

The electric heating assembly 34a comprises an electric heating element 34a1 and a supporting frame 34a2, the electric heating element 34a1 is fitted into the supporting frame 34a2 and is arranged to correspond to the filter piece 36 to atomize the cigarette liquid.

The power connecting assembly 34b comprises an insulation ring 34b1 and a needle electrode 34b2, the needle electrode 34b2 passes through the insulation ring 34b1 and the supporting frame 34a2 to be finally electrically connected to the electric heating element 34a1.

The battery control assembly 20 is connected to a bottom of the supporting frame 34a2 through a fixation seat 37.

The exterior longitudinal flat surface 32a of the liquid storage cup 32 is a rectangle.

The width of the arc-shaped slit a2 is from 0.05 mm to 0.8 mm.

In use, the vaporizer unit 34 produces vapor, the produced vapor passes through the air passage a1 to enter into the vapor flow passage a3, and then diffuses into the arc-shaped slit a2. Some of the produced vapor will be condensed to form residual liquid due to temperature difference, and the condensed residual liquid will be adsorbed in the arc-shaped slit a2 due to the narrow space of the arc-shaped slit a2, thus preventing the condensed residual liquid from being inhaled into the user's mouth. From the above, by the arrangement of the vapor flow passage a3 and the arc-shaped slit a2, the cotton-free electronic cigarette of the present invention solves the problem of liquid spill in existing cotton-free electronic cigarettes.

All the above are the preferred embodiments of the present invention, and the invention is intended to cover various modifications and equivalent arrangements included within the scope of the invention.

What is claimed is:

1. A cotton-free electronic cigarette preventing liquid spill, comprising a mouthpiece assembly, a battery control assembly and a vaporizer assembly, the mouthpiece assembly and the battery control assembly being respectively connected to two ends of the vaporizer assembly, characterized in that the vaporizer assembly comprises:

an outer sleeve, the outer sleeve being a pipe having an inner diameter larger than an outer diameter of a liquid storage cup of the cotton-free electronic cigarette, the liquid storage cup, being a cylinder having a segmental-circular cross section formed by an exterior longitudinal flat surface, an exterior surface of an outlet end of the liquid storage cup being provided with a bayonet, the bayonet being configured to be fitted into a heat insulation sleeve, a vaporizer unit, the vaporizer unit comprising an electric heating assembly and a power connecting assembly, and the heat insulation sleeve, the heat insulation sleeve having a tubular structure;

the liquid storage cup stores cigarette liquid therein, an opening of the liquid storage cup is provided with a liquid percolation piece and a filter piece; the vaporizer unit is placed inside the heat insulation sleeve; the exterior longitudinal flat surface of the liquid storage cup forms an air passage when the bayonet of the liquid storage cup is fitted into the heat insulation sleeve; the liquid storage cup is sheathed with the outer sleeve, an inner wall of the outer sleeve and an exterior arc surface of the liquid storage cup forms an arc-shaped slit, the arc-shaped slit being used for preventing spill of residual condensed cigarette liquid; the inner wall of the outer sleeve and the exterior longitudinal flat surface of the liquid storage cup forms a vapor flow passage, the vapor flow passage is interconnected to the arc-shaped slit; the mouthpiece assembly is fixed to one end of the outer sleeve to seal an outlet of the arc-shaped slit, such that an inhalation hole of the mouthpiece assembly is interconnected to the vapor flow passage.

2. The cotton-free electronic cigarette preventing liquid spill of claim 1, characterized in that the mouthpiece assembly is mainly consisted of a mouthpiece, the mouthpiece is inserted into said one end of the outer sleeve, the inhalation hole of the mouthpiece assembly is arranged in the middle of the mouthpiece, an interior end of the mouthpiece has an annular groove, the annular groove is positioned between the inhalation hole and the vapor flow passage so as to further prevent liquid spill.

3. The cotton-free electronic cigarette preventing liquid spill of claim 2, characterized in that the segmental-circular cross section of the liquid storage cup which is formed by the exterior longitudinal flat surface is encircled by the arc-shaped slit.

4. The cotton-free electronic cigarette preventing liquid spill of claim 3, characterized in that the outer sleeve receives the battery control assembly to form a disposable electronic cigarette.

5. The cotton-free electronic cigarette preventing liquid spill of claim 4, characterized in that the electric heating assembly comprises an electric heating element and a supporting frame, the electric heating element is fitted into the supporting frame and is arranged to correspond to the filter piece to atomize cigarette liquid.

6. The cotton-free electronic cigarette preventing liquid spill of claim 5, characterized in that the power connecting assembly comprises an insulation ring and a needle electrode, the needle electrode passes through the insulation ring and the supporting frame to be finally electrically connected to the electric heating element.

7. The cotton-free electronic cigarette preventing liquid spill of claim 6, characterized in that the battery control assembly is connected to a bottom of the supporting frame through a fixation seat.

8. The cotton-free electronic cigarette preventing liquid spill of claim 7, characterized in that the exterior longitudinal flat surface of the liquid storage cup is a rectangle.

9. The cotton-free electronic cigarette preventing liquid spill of claim 8, characterized in that the width of the arc-shaped slit is from 0.05 mm to 0.8 mm.

* * * * *